United States Patent [19]

Prisbe et al.

[11] Patent Number: 4,590,269

[45] Date of Patent: May 20, 1986

[54] PROCESS FOR PREPARING THE CYCLIC PHOSPHATE ESTER OF SUBSTITUTED 9-(1,3-DIHYDROXY-2-PROPOXYMETHYL)-PURINES

[75] Inventors: Ernest J. Prisbe, Los Altos; Daniel P. C. McGee, Mountain View, both of Calif.

[73] Assignee: Syntex (U.S.A.) Inc., Palo Alto, Calif.

[21] Appl. No.: 594,508

[22] Filed: Mar. 29, 1984

[51] Int. Cl.⁴ .................... C07D 473/18; A61K 31/52
[52] U.S. Cl. .................................... 544/276; 544/277
[58] Field of Search ............... 260/937; 544/276, 277; 514/261, 262

[56] References Cited

U.S. PATENT DOCUMENTS 4,087,490  5/1978  Lesser et al. .................... 260/937

Primary Examiner—Nicholas S. Rizzo
Attorney, Agent, or Firm—Annette M. Moore; Tom M. Moran

[57] ABSTRACT

An improved process for preparing the cyclic phosphate ester of substituted 9-(1,3-dihydroxy-2-propoxymethyl)purines which are useful as antiviral agents.

18 Claims, No Drawings

PROCESS FOR PREPARING THE CYCLIC PHOSPHATE ESTER OF SUBSTITUTED 9-(1,3-DIHYDROXY-2-PROPOXYMETHYL)PURINES

BACKGROUND OF THE INVENTION

1. Field of the Invention

This invention relates to a process for preparing the cyclic phosphate ester of substituted 9-(1,3-dihydroxy-2-propoxymethyl)purines which are useful as antiviral agents.

2. Related Disclosure

The compound 9-(1,3-dihydroxy-2-propoxymethyl)-guanine cyclic phosphate ester is a potent antiviral agent and has been prepared by methods disclosed in European Patent Application No. 74,306. The present invention relates to an improved process for preparing the cyclic phosphate ester of 9-(1,3-dihydroxy-2-propoxymethyl)guanine and of 2,6-diamino-9-(1,3-dihydroxy-2-propoxymethyl)purine. The present process involves a two step reaction which eliminates the multiple separation and purification steps required in previous known processes. The instant process also results in increased yields of the product.

SUMMARY OF THE INVENTION

The invention relates to a process for preparing the cyclic phosphate ester of 9-(1,3-dihydroxy-2-propoxymethyl)guanine and of 2,6-diamino-9-(1,3-dihydroxy-2-propoxymethyl)purine and the pharmaceutically acceptable salts thereof which comprises reacting a phosphorylating agent with the dihydroxy compound complexed with a Lewis acid to form a compound of the formula

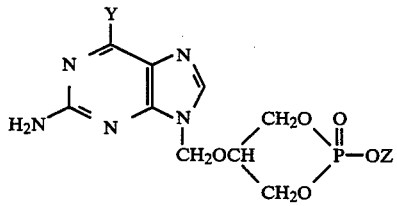

wherein Y is hydroxy or amino and Z is hydrogen, an optionally substituted hydrocarbon or a pharmaceutically acceptable cation.

DETAILED DESCRIPTION AND PREFERRED EMBODIMENT

Broadly, the present invention relates to a process for preparing compounds of the formula

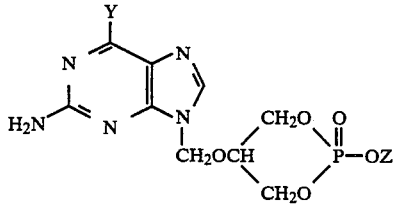

which comprises reacting a phosphorylating agent with a Lewis acid complex of a compound of the formula

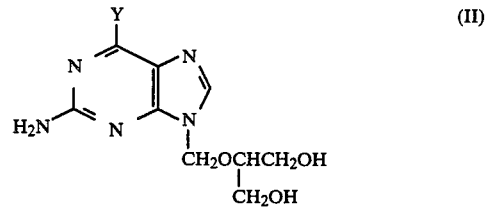

wherein Y is hydroxy or amino and Z is hydrogen, an optionally substituted hydrocarbon group or a pharmaceutically acceptable cation.

More specifically, the invention relates to a process wherein the phosphorylating agent is a phosphoryl halide, a pyrophosphoryl halide or an optionally substituted hydrocarbon phosphorodichloridate.

One preferred embodiment of the present invention is preparing a compound of formula (I) wherein Y is hydroxy.

Another preferred embodiment is preparing compounds of formula (I) wherein Z is hydrogen or a pharmaceutically acceptable cation.

Still another preferred embodiment is a process wherein the phosphorylating agent is a phosphoryl halide or a pyrophosphoryl halide.

As used in the specification and appended claims, unless specified to the contrary, the following terms have the meaning indicated.

The term "pharmaceutically acceptable cation" refers to those cations which possess the biological effectiveness and properties of the free compound and which are not biologically or otherwise undesirable. Suitable cations may be inorganic or organic cations. Inorganic cations include ammonium, the ions of sodium, potassium, lithium, calcium, magnesium, and the like. Particularly preferred are the potassium ion, the sodium ion and ammonium. Cations derived from organic non-toxic bases include cations of primary, secondary, and tertiary amines, substituted amines including naturally occurring substituted amines and cyclic amines such as isopropylamine, trimethylamine, diethylamine, triethylamine, tripropylamine, ethanolamine, 2-dimethylaminoethanol, morpholine 2-diethylaminoethanol, tromethamine, dicyclohexylamine, ethylenediamine, glucosamine, N-methylglucamine, piperazine, piperidine, N-ethylpiperidine, and the like. Preferred organic non-toxic cations are those derived from N-methylglucamine, diethylamine, piperazine, morpholine, and dicyclohexylamine. Other useful amines are those disclosed in J. Pharm Sci, 66, 1(1977) incorporated herein by reference.

The term "Lewis acid" refers to a substance which can accept an electron pair and which can form a complex. Examples of "Lewis acids" are stannic chloride, titanium tetrachloride, the trimethylsilyl ester of trifluoromethanesulfonic acid, boron trifluoride and the like.

The term "halide" refers to chloride and bromide.

The term "optionally substituted hydrocarbon" refers to groups which consist solely of hydrogen and carbon and which may be substituted by groups containing atoms other than hydrogen and carbon. Examples of "optionally substituted hydrocarbons" are phenyl, nitrophenyl, methylphenyl, methyl, ethyl, cyanoethyl and the like.

It is understood that the definition of Y as hydroxy encompasses the tautomeric oxo form as well.

The process of the present invention is depicted by the Reaction Sequence shown below.

REACTION SEQUENCE

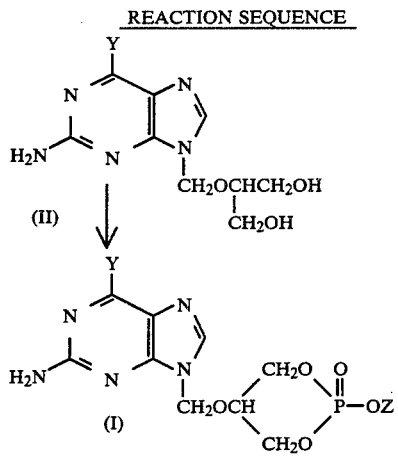

wherein Y is amino or hydroxy and Z is hydrogen, an optionally substituted hydrocarbon or a pharmaceutically acceptable cation.

The compounds of formula (I) are prepared by reacting a phosphorylating agent with a solution of compound of formula (II) complexed with a Lewis acid. To a suspension of compound of formula (II) in a solvent such as acetonitrile, dioxane, ethyl acetate and the like, preferably acetonitrile, is added a Lewis acid such as stannic chloride, titanium tetrachloride and the like. The mixture is stirred at 10° C. to 35° C., preferably at room temperature, until compound of formula (II) is completely dissolved, preferably for ¾ to ½ hours. A phosphorylating agent in a solvent such as anhydrous acetonitrile, dioxane, ethyl acetate and the like is added at about room temperature over about ½ hour to 3 hours, preferably over about 1½ hours, to the solution of compound of formula (II) complexed with the Lewis acid. After addition is complete, the reaction is stirred at about room temperature for about 30 minutes to 3 hours, preferably 1 hour to 2 hours. The solution is then concentrated in vacuo and the residue, dissolved in water, is absorbed onto an activated charcoal column, washed with water then eluted. The eluent is evaporated to dryness and the residue is recovered by recrystallization to give compound of formula (I) as the monoammonium salt.

When the phosphorylating agent is a phosphoryl halide or a pyrophosphoryl halide compounds of formula (I) are prepared wherein Z is hydrogen or a pharmaceutically acceptable cation.

When the phosphorylating agent is an optionally substituted hydrocarbon phosphorodichloridate compounds of formula (I) are prepared wherein Z is an optionally substituted hydrocarbon. These compounds may be converted to compounds of formula (I) wherein Z is hydrogen or a pharmaceutically acceptable cation by methods known in the art such as by hydrolysis, for example, basic hydrolysis using, e.g., ammonium hydroxide or an alkali metal hydroxide such as sodium hydroxide.

Compounds of formula (I) wherein Z is hydrogen, i.e., the free acid, may be prepared by passing a solution of a compound of formula (I) wherein Z is a cation such as an alkali metal ion, e.g. the sodium or potassium ion through an ion exchange resin such as Dowex 50-X8 available from Dow Chemical Co.

Compounds of formula (I) wherein Z is a cation, particularly ammonium ion, may be prepared in situ as illustrated in the Reaction Sequence. The ammonium salt may be transformed into other desired salts by passing a solution containing the ammonium salt through an appropriate cation exchange resin such as a Dowex 50 resin, available from Dow Chemical Co., containing the desired cation.

Alternatively, compounds of formula (I) wherein Z is a pharmaceutically acceptable cation may be prepared by first forming the free acid as is described above and then reacting the free acid with the appropriate cation source.

Compounds of formula (II) wherein Y is hydroxy is prepared by the method described in U.S. Pat. No. 4,355,032 which is incorporated herein by reference. Compounds of formula (II) wherein Y is amino may be prepared by the above method except that the acetylguanine is replaced by acetyl protected 2-amino-6-chloropurine. The 6-chloro group is replaced by amino by treatment with a base such as methanolic ammonia or methanolic ammonium hydroxide.

The phosphorylating agents are available from, i.a., Aldrich Chemical Co. and Sigma Chemical Co.

The following specific examples are illustrative of the present invention and should not be considered as limitative thereof.

EXAMPLE 1

To a stirred suspension of 9-(1,3-dihydroxy-2-propoxymethyl)guanine (2.0 g) in dry acetonitrile (1.5 l) was added stannic chloride (1.3 ml). The mixture was stirred at 21° C. for 1 hour during which time all 9-(1,3-dihydroxy-2-propoxymethyl)guanine dissolved. To this stirred solution was added, dropwise over 1½ hours, a solution of pyrophosphoryl chloride (3.4 ml) in acetonitrile (0.6 l). When addition was complete the solution was stirred an additional 2 hours at 21° C. before being neutralized (pH ~6) by the addition of saturated aqueous sodium bicarbonate. The precipitated salts were filtered off.

The filtrate was concentrated in vacuo to ~50 ml and applied onto a column of activated charcoal (115 g). The column was first washed with 4 l of water to remove inorganic salts, then with 5% ammonium hydroxide in 50% aqueous ethanol to elute the cyclic phosphate ester of 9-(1,3-dihydroxy-2-propoxymethyl)guanine.

Eluent containing pure cyclic phosphate ester of 9-(1,3-dihydroxy-2-propoxymethyl)guanine was pooled and evaporated in vacuo. The residue was crystallized from water/ethanol to give pure cyclic phosphate ester of 9-(1,3-dihydroxy-2-propoxymethyl)guanine ammonium salt (1.30 g) m.p. 240° C. darkens without melting.

Similarly, substituting 2,6-diamino-9-(1,3-dihydroxy-2-propoxymethyl)purine for 9-(1,3-dihydroxy-2-propoxymethyl)guanine and proceeding as above, the cyclic phosphate ester of 2,6-diamino-9-(1,3-dihydroxy-2-propoxymethyl)purine is obtained.

EXAMPLE 2

To the stirred solution of 2,6-diamino-9-(1,3-dihydroxy-2-propoxymethyl)purine (650 mg) and stannic chloride (300 μl) in dry acetonitrile (250 ml) was added dropwise over 3½ hours a solution of phosphoryl chloride (240 μl) in acetonitrile (200 ml). Additional stannic chloride (100 μl) followed by a solution of phosphoryl chloride (240 μl) in acetonitrile (10 ml) was then added to the solution. The reaction mixture was stirred at room temperature overnight and then neutralized with aqueous Na₂CO₃. The resulting precipitate was removed by filtration. The aqueous phase was evaporated to a reduced volume (100 ml) and applied onto a column of activated charcoal (42 gm). The column was washed with water (900 ml) and then eluted with 5% ammonium hydroxide in 50% aqueous ethanol. The fractions were pooled and evaporated. The solid was crystallized from methanol/n-butanol to give pure cyclic phosphate ester of 2,6-diamino-9-(1,3-dihydroxy-2-propoxymethyl)purine ammonium salt (230 mg), m.p. >300° C. dec.

EXAMPLE 3

A compound of formula (I), prepared in accordance with Examples 1 or 2 is dissolved in water and is transformed into other corresponding salts by passing the salt as a solution through DOWEX 50 resin with the corresponding cation desired on the resin.

Similarly, using the above procedure one obtains, for example, the following compounds:
cyclic phosphate ester of 9-(1,3-dihydroxy-2-propoxymethyl)guanine trimethylammonium salt;
cyclic phosphate ester of 9-(1,3-dihydroxy-2-propoxymethyl)guanine diethylammonium salt;
cyclic phosphate ester of 2,6-diamino-9-(1,3-dihydroxy-2-propoxymethyl)purine cyclohexylammonium salt;
cyclic phosphate ester of 9-(1,3-dihydroxy-propoxymethyl)guanine morpholinium salt; and
cyclic phosphate ester of 2,6-diamino-9-(1,3-dihydroxy-2-propoxymethyl)purine triethylammonium salt.

What is claimed is:

1. A process for preparing a compound of the formula

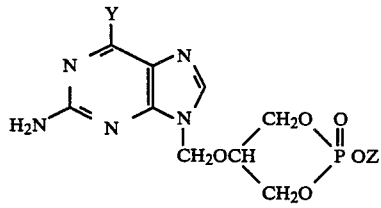

wherein y is amino or hydroxy and Z is hydrogen, an optionally substituted hydrocarbon or a pharmaceutically acceptable cation which comprises reacting a Lewis acid complex of the compound of the formula

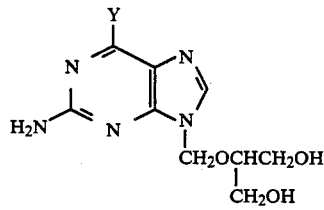

with a phosphorylating agent.

2. The process of claim 1 wherein Y is amino.
3. The process of claim 1 wherein Y is hydroxy.

4. The process of claim 1 wherein the Lewis acid is stannic chloride, titanium chloride, boron trifluoride or the trimethylsilyl ester of trifluoromethanesulfonic acid.

5. The process of claim 4 wherein the Lewis acid is stannic chloride.

6. The process of claim 1 wherein the phosphorylating agent is a pyrophorphoryl halide or a phosphoryl halide.

7. The process of claim 6 wherein the pyrophosphoryl halide is pyrophosphoryl chloride.

8. The process of claim 6 wherein the phosphoryl halide is phosphoryl chloride.

9. The process of claim 1 which further comprises hydrolyzing compound of formula (I) wherein Z is an optionally substituted hydrocarbon to form a compound of formula (I) wherein Z is hydrogen or a pharmaceutically acceptable cation.

10. A process for preparing a compound of the formula

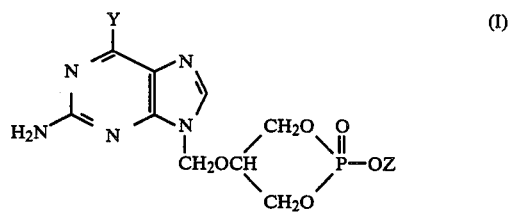

wherein Y is amino or hydroxy and Z is hydrogen, an optionally substituted hydrocarbon or a pharmaceutically acceptable cation which comprises forming a complex of a compound of the formula

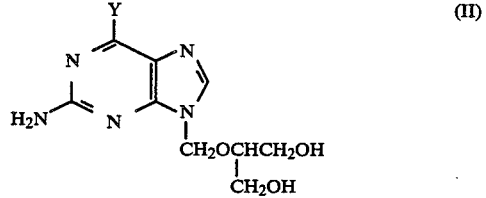

with a Lewis acid and reacting the complex so formed with a phosphorylating agent.

11. The process of claim 10 wherein Y is amino.
12. The process of claim 10 wherein Y is hydroxy.
13. The process of claim 10 wherein the Lewis acid is stannic chloride, titanium chloride, boron trifluoride or the trimethylsilyl ester of trifluoromethanesulfonic acid.
14. The process of claim 13 wherein the Lewis acid is stannic chloride.
15. The process of claim 10 wherein the phosphorylating agent is a pyrophorphoryl halide or a phosphoryl halide.
16. The process of claim 15 wherein the pyrophosphoryl halide is pyrophosphoryl chloride.
17. The process of claim 15 wherein the phosphoryl halide is phosphoryl chloride.
18. The process of claim 10 which further comprises hydrolyzing compound of formula (I) wherein Z is an optionally substituted hydrocarbon to form a compound of formula (I) wherein Z is hydrogen or a pharmaceutically acceptable cation.

* * * * *